(12) United States Patent
Wikfors

(10) Patent No.: US 10,376,814 B2
(45) Date of Patent: Aug. 13, 2019

(54) IMPACT CENTRIFUGAL SEPARATOR AND ASSOCIATED METHODS FOR FRACTION COLLECTION IN SUPERCRITICAL FLUID SYSTEMS

(71) Applicant: Agilent Technologies, Inc., Santa Clara, CA (US)

(72) Inventor: Edwin E. Wikfors, Landenberg, PA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 15/542,925

(22) PCT Filed: Jan. 30, 2015

(86) PCT No.: PCT/US2015/013889
§ 371 (c)(1),
(2) Date: Jul. 11, 2017

(87) PCT Pub. No.: WO2016/122633
PCT Pub. Date: Aug. 4, 2016

(65) Prior Publication Data
US 2018/0015390 A1    Jan. 18, 2018

(51) Int. Cl.
*B01D 1/14* (2006.01)
*B04B 7/00* (2006.01)
(Continued)

(52) U.S. Cl.
CPC ............ *B01D 15/40* (2013.01); *B01D 1/14* (2013.01); *B01D 11/0203* (2013.01);
(Continued)

(58) Field of Classification Search
CPC ...... B01D 15/40; B01D 11/0203; B01D 1/14; B01D 46/0031; B01D 11/0292;
(Continued)

(56) References Cited

U.S. PATENT DOCUMENTS 4,478,720 A    10/1984   Perrut
4,964,898 A * 10/1990   Toda ................. B01D 45/02
                                                                           55/323
(Continued)

FOREIGN PATENT DOCUMENTS

CN         102216769 A    10/2011
CN         103249462 A    8/2013
(Continued)

OTHER PUBLICATIONS

International Search Report and Written Opinion dated Sep. 23, 2015 from related International Application No. PCT/US2015/013889.
Extended European Search Report issued in counterpart EP Application No. 15880523.4 dated Aug. 16, 2018 (eight (8) pages).

*Primary Examiner* — David C Mellon

(57) ABSTRACT

A separator (e.g. an impact centrifugal separator) is for use in collection of liquid portions of a bi-phasic flowstream in a supercritical fluid system. A separator chamber defines an interior space, surrounded by a spiral channel and that has an exit at a lower portion of the separator chamber. A flowstream director (e.g. an entry lube) focuses the flowstream so that the flowstream impacts a wail of the spiral channel at an angle that promotes coalescence of the liquid component. The spiral channel may promote further coalescence of the liquid portions within the constraining spiral channel after impact. A central director may be included in the interior space of the separator chamber to promote flow of the gaseous component toward the exit. A dripper may be included in fluid communication with the spiral channel, for example, in the exit and to direct the coalesced liquid into a collection vessel.

20 Claims, 4 Drawing Sheets

(51) Int. Cl.
*B01D 11/02* (2006.01)
*B01D 15/24* (2006.01)
*B01D 15/40* (2006.01)
*B01D 19/00* (2006.01)
*B01D 46/00* (2006.01)
*B04B 11/06* (2006.01)
*G01N 30/82* (2006.01)
*G01N 30/84* (2006.01)
*G01N 30/88* (2006.01)

(52) U.S. Cl.
CPC ........ *B01D 11/0292* (2013.01); *B01D 15/247* (2013.01); *B01D 19/0057* (2013.01); *B01D 46/0031* (2013.01); *G01N 30/82* (2013.01); *B04B 7/00* (2013.01); *B04B 11/06* (2013.01); *G01N 30/84* (2013.01); *G01N 2030/8809* (2013.01)

(58) Field of Classification Search
CPC .... B01D 21/26; B01D 21/262; B01D 21/265; B01D 21/267; B01D 19/0057; B01D 15/247; G01N 30/84; G01N 30/82; G01N 2030/8809; B04B 11/06; B04B 7/00; B04B 5/12; B04C 2003/003; B04C 2003/006; B04C 3/06; B04C 5/081
See application file for complete search history.

(56) References Cited

U.S. PATENT DOCUMENTS

| | | |
|---|---|---|
| 6,162,162 A | 12/2000 | Robey |
| 6,413,428 B1 | 7/2002 | Berger et al. |
| 6,458,273 B1 | 10/2002 | Krakover et al. |
| 8,262,760 B2 | 9/2012 | Fogelman et al. |
| 8,327,725 B2 | 12/2012 | Kanomata |
| 2002/0144949 A1 | 10/2002 | Berger et al. |
| 2008/0164194 A1 | 7/2008 | Hedberg |
| 2009/0114607 A1* | 5/2009 | Lean ................ B03B 5/626 210/779 |
| 2013/0008859 A1 | 1/2013 | Witt |
| 2013/0180404 A1 | 7/2013 | Fogelman et al. |
| 2014/0190890 A1 | 7/2014 | Sidhu et al. |
| 2014/0283688 A1 | 9/2014 | Fogelman et al. |
| 2015/0290369 A1* | 10/2015 | Hamman ............ A61M 1/0281 435/2 |
| 2016/0339359 A1* | 11/2016 | Hallot ................ B01D 19/0036 |

FOREIGN PATENT DOCUMENTS

| | | |
|---|---|---|
| CN | 103582515 A | 2/2014 |
| EP | 2168647 A1 | 3/2010 |
| WO | 2014012962 A1 | 1/2014 |

* cited by examiner

IMPACT CENTRIFUGAL SEPARATOR AND ASSOCIATED METHODS FOR FRACTION COLLECTION IN SUPERCRITICAL FLUID SYSTEMS

RELATED APPLICATIONS

This application is the national stage under 35 U.S.C. 371 of International Application No. PCT/US 2015/013889, filed Jan. 30, 2015, titled "IMPACT CENTRIFUGAL SEPARATOR AND ASSOCIATED METHODS FOR FRACTION COLLECTION IN SUPERCRITICAL FLUID SYSTEMS", the entire contents of which are incorporated herein by reference.

FIELD

The field of the present embodiments is directed to fraction collection in supercritical fluid systems including supercritical fluid chromatography (SFC) and supercritical fluid extraction (SFE).

BACKGROUND

Generally, packed column chromatography systems separate analytes of a sample using a separation unit, such as a chromatographic column. For example, a sample containing various analytes, such as chemical compounds, or other sample constituents, dissolved in a solvent solution may be injected into a mobile phase fluid stream with an injection valve, where the mobile phase typically comprises one or more solvents. The sample-containing mobile phase flows through the chromatographic column which selectively retains the analytes from the sample. The analytes from the sample experience a differential retention with the column's stationary phase, e.g., using packing material or sorbent within the chromatographic column, and the relative elution strength of the mobile phase. The separated analytes may then be directed to a detector for detection and analysis, where each of the analytes emerges from the chromatographic column at a different time corresponding to the respective differential retention of that analytes within the chromatographic column. Detection over time results in "peaks" respectively corresponding to the analytes of the sample, where magnitude of each peak correlates to the amount of the corresponding analytes in the sample. In preparative chromatography systems, the separated sample constituents may be collected by various fraction collection devices.

Typically, the mobile phase is a mixture of solvents provided by corresponding pumping systems. The solvents include at least a strong solvent and a weak solvent referring to the solvents relative elution strength in relation to each other and to the stationary phase being used. The strong solvent favors a partitioning of the sample components into the mobile phase, thus lessening retention, or providing faster transiting of the chromatographic column. The weak solvent favors partitioning of the sample components on the column's stationary phase thus increasing retention, and may serve to moderate the effects of the strong solvent. Attempts are made to balance the mobile phase composition or ratio between the strong and weak solvents in order to provide an acceptable comprise between speed of the chromatography operation and quality of the analytical results.

One type of chromatography system is Supercritical Fluid Chromatography (SFC). SFC with packed columns typically uses an organic solvent termed a modifier, such as methanol, ethanol, propanol, etc., as the strong solvent and highly compressed dense gas, most commonly carbon dioxide ($CO_2$), as the weak solvent. It can be noted that while the name of the technique, SFC, implies use of fluids in a supercritical state, the actual use includes fluids that while dense, are not necessarily supercritical.

Supercritical Fluid Extraction (SFE) is the process of separating one or more components (the extractants) from another (the matrix) using fluids similar to a SFC mobile phase as the extracting solvents. Extraction is usually from a solid matrix, but can also be from liquids. SFE can be used as a sample preparation step for analytical purposes, or on a larger scale to either strip unwanted material from a product or collect a desired product. Again, carbon dioxide ($CO_2$) is the most used supercritical fluid, sometimes modified by co-solvents such as ethanol or methanol.

The properties of a supercritical fluid can be altered by varying the pressure and temperature, allowing selective extraction. A typical SFE system includes a pumping system for the $CO_2$, and any co-solvents, a pressure cell to contain the sample, the ability to maintain pressure in the system and a collecting vessel or vessels. The liquid may be pumped to a heating zone, where its temperature may be raised to true supercritical conditions. It then passes into the extraction vessel, where it rapidly diffuses into the solid matrix and dissolves the material to be extracted. The dissolved material is swept from the extraction cell into a separator at lower pressure, and the extracted materials are removed.

Various sample collection approaches exist and are disclosed in the following documents: "Sample collection container, sample collection apparatus, and sample collection method in supercritical fluid system", U.S. Pat. No. 8,327,725 to Kanamoto which is directed to a vial cap based system; "Apparatus and method for preparative supercritical fluid chromatography", U.S. Pat. No. 6,413,428 to Berger which is directed to a pressurized tube collector; "Fractionation process for mixtures by elution chromatography with liquid in supercritical state and installation for its operation", U.S. Pat. No. 4,478,720 to Perrut which is directed to high pressure cyclone collections; "Process Flowstream Collection System", U.S. Pat. No. 8,262,760 to Fogelman which is directed to a near atmospheric separator; and "Collection system for purification flowstreams", U.S. Publication No. 2014/0190890 to Sidhu which is directed to utilizing a specialized dripper within a pressurized separator. U.S. Publication No. 2014/0283688 to Fogleman et al. entitled "Self Cleaning Gas-Liquid Separator for Serial or Parallel Collection of Liquid Fractions" is directed to a porous coalescence filter used as part of a gas-liquid separator.

Many of these prior approaches generally contain the effluent of the separation under some modest, or in some cases, a controlled, pressure. After the separation in a containing vessel, the $CO_2$ is generally removed from the opposite end of the liquid exit, or opposite the collected liquid pool. These conventional separators generally operate in either batch (chiral) mode, or sequential (library) mode. Batch mode operation often obviates the need for strong cleaning of the collector as the same compound is seen on each (one of many) collectors for avoidance of carryover. Sequential collectors need to generally exhibit a high degree of self-cleaning with minimum carry over or broadening of fluidic elements as each collection may immediately change to the next fraction/vessel. Further, successful collection of sequential fractions cut downstream of the separator may require a highly deterministic (in time) way of recognizing a fraction start and stop. Broadening of a peak within the separator prior to the fraction cut can cause adjacent peaks to merge resulting in loss of both purity and recovery of the collected fraction.

It is desirable to provide for the collection of fractions without requiring a contained vessel to separate the gaseous component, requiring external pressure control to reduce aerosol formation, or requiring specifically adapted collection vessels, while additionally allowing downstream fraction cuts.

BRIEF DESCRIPTION OF THE DRAWINGS

The representative embodiments are best understood from the following detailed description when read with the accompanying drawing figures. Wherever applicable and practical, like reference numerals refer to like elements.

DETAILED DESCRIPTION

In the following detailed description, for purposes of explanation and not limitation, illustrative embodiments disclosing specific details are set forth in order to provide a thorough understanding of embodiments according to the present teachings. However, it will be apparent to one having had the benefit of the present disclosure that other embodiments according to the present teachings that depart from the specific details disclosed herein remain within the scope of the appended claims. Moreover, descriptions of well-known devices and methods may be omitted so as not to obscure the description of the example embodiments. Such methods and devices are within the scope of the present teachings.

Generally, it is understood that as used in the specification and appended claims, the terms "a", "an" and "the" include both singular and plural referents, unless the context clearly dictates otherwise. Thus, for example, "a device" includes one device and plural devices.

As used in the specification and appended claims, and in addition to their ordinary meanings, the terms "substantial" or "substantially" mean to within acceptable limits or degree. For example, "substantially cancelled" means that one skilled in the art would consider the cancellation to be acceptable. As a further example, "substantially removed" means that one skilled in the art would consider the removal to be acceptable.

As used in the specification and the appended claims and in addition to its ordinary meaning, the term "approximately" means to within an acceptable limit or amount to one having ordinary skill in the art. For example, "approximately the same" means that one of ordinary skill in the art would consider the items being compared to be the same.

By theoretical definition, a supercritical fluid is any substance at a temperature and pressure above its critical point, where distinct liquid and gas phases do not exist. For the purposes of this disclosure, the term supercritical fluid shall be deemed to additionally include fluids comprising a dense gas below the critical point, yet still miscible with the liquid organic modifier and behaving as a mono-phasic fluid. This definition is compatible with the common usage of carbon dioxide based 'Supercritical Fluid' chromatography systems in use today.

The preferred embodiments may be used in the collection process of liquid phase samples or flow from a flowstream. The liquids can be from all or part of a process flow system containing a liquefied gas or supercritical fluid under pressure mixed with a liquid that collects the liquid phase separated from the flowstream essentially at atmospheric pressure. The preferred embodiments can be use for preparative chromatography and extraction using supercritical and near critical materials.

Figure 1:
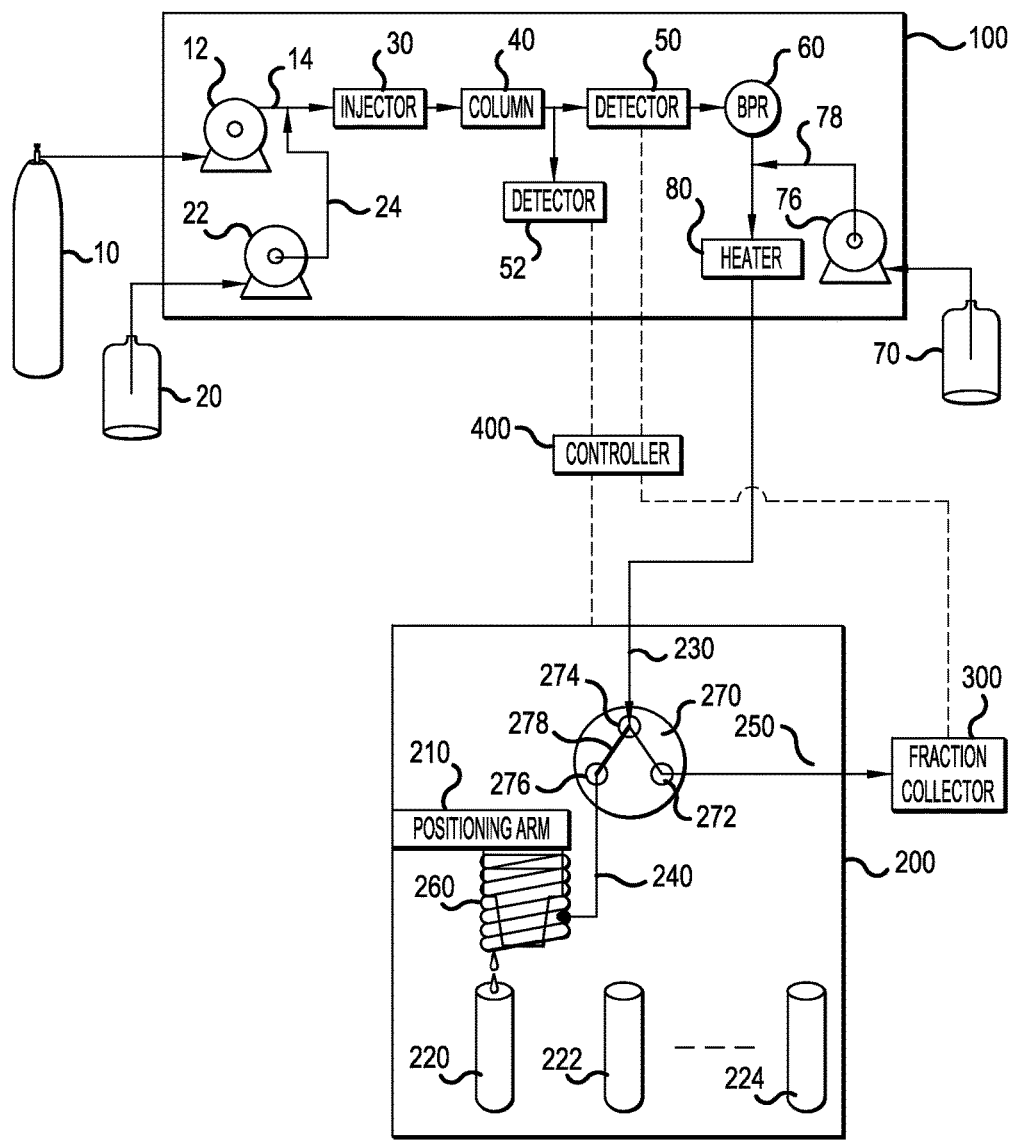
FIG. 1 is a simplified block diagram of a chromatography system including a robotic fraction collector, according to a representative embodiment.

FIG. 1 is a simplified block diagram of a chromatography system, according to a representative embodiment. Referring to FIG. 1, an embodiment for collecting fractions from the effluent exiting an exemplary supercritical fluid chromatography (SFC) system 100 will be described. The SFC system 100 utilizes a mobile phase that generally includes a non-polar component such as carbon dioxide in a reservoir 10 and a polar organic liquid from a reservoir 20 pumped by respective pumps 12 and 22. The pumps 12 and 22 are illustrated as single pumps but could additionally encompass well known features (not shown) such as chillers, dampers, and additional pumps to facilitate increased efficiencies or delivery attributes. The metered and pressurized fluids exit from pumps 12 and 22 in conduits 14 and 24 respectively before joining to become the chromatographic mobile phase.

The chromatographic mobile phase flows through the injector 30. The injector 30 will inject aliquots of a sample to be separated into the chromatographic mobile phase. The injector 30 may be implemented by automated liquid sampling systems or valve based injection approaches, as would be appreciated by those skilled in the art. After leaving the injector 30, the chromatographic mobile phase, containing an aliquot of sample, will be directed to a separation column 40. The separation column 40 includes a packed stationary phase that separates sample constituents via differential affinities between the stationary phase of the separation column 40 and the chromatographic mobile phase. The separated sample constituents exit the separation column 40 within the chromatographic mobile phase before being directed to one or more detectors 50 and 52, for example. The detector 52, optionally included as part of the SFC System 100, may be a destructive detector such as a mass spectrometer.

The detector 50 is exemplarily included in the SFC System 100 as a non-destructive detector such as a UV diode array detector or chiral based detector using techniques such as circular dichroism. One or more detectors such as detectors 50 and 52 detect sample constituents in the effluent from separation column 40 and provide signals representing the sample constituents to a controller 400. The detectors 50 and 52 could each incorporate multiple individual detectors of various types without departing from the present teachings. After leaving the detector 50, the column effluent passes through a back pressure regulator (BPR) 60. The back pressure regulator 60 keeps the upstream pressure above a pressure where the chromatographic mobile phase is compatible with the detectors 50 and 52, and remains monophasic. This upstream pressure maintained by the back pressure regulator 60 may operate in an exemplary, range of 90 bar to 200 bar. An optional pump 76 may be utilized to pump an additional makeup fluid, from reservoir 70 through conduit 78 to be joined with the column effluent. The makeup fluid is generally comprised of an organic liquid such as methanol, possibly entrained with additives to enhance detector operation. The junction point of conduit 78 is exemplarily shown as downstream of back pressure regulator 60, but could equivalently be located at points upstream of back pressure regulator 60 and downstream of separation column 40.

After exiting back pressure regulator 60, the column effluent containing sample constituents and chromatographic mobile phase components drops in pressure and becomes bi-phasic. The carbon dioxide expands and cools becoming un-miscible with the organic liquid components upon leaving the back pressure regulator 60. An optional heater 80 may be used to restore some of the heat lost in the expansion of the exiting carbon dioxide. The expanded chromatographic effluent, exiting the back pressure regulator 60 and the heater 80 is then directed to one or more fraction collectors 200, 300.

The fraction collectors 200, 300 are informed of the presence of a separated sample constituent, detected by one or more detectors 50, 52, exemplarily through controller 400. In various embodiments, the fraction collectors 200, 300 are exemplarily of similar type and include a collect divert valve 270. Collect divert valve 270 incorporates two positions to either a collect position whereby the expanded effluent entering via the conduit 230 connected to a valve port 274 is directed to port 276 and conduit 240, or to a divert position where the expanded effluent is directed to a conduit 250 connected to the valve port 272. The conduit 250 exits the fraction collector 200 and may be directed to one or more subsequent fraction collectors 300, detectors, or waste. The fraction collector 200 may further include a plurality of collection vessels 220, 222, 224 and a positioning arm 210 to locate an impact centrifugal separator 260 above a particular collection vessel. While three collection vessels 220, 222, 224 are depicted, the number of vessels addressable via positioning arm 210 is generally much greater.

A decision to collect an aliquot or fraction of the expanded effluent can be made by controller 400 based upon a signal from one or more of the detectors 50, 52, or be based upon a time, often relative to the injection of a sample aliquot by injector 30. When the controller 400 has determined that the fraction desired to be collected is present in the conduit 230 at valve port 274, the valve 270 is directed to switch the flowstream from the divert position to the collect position. This switch is exemplarily shown as moving a groove 278 connecting valve port 274 and valve port 272 to a different position connecting valve port 274 to valve port 276. With the valve 270 in the collect position, thereby connecting ports 274 and 276 with groove 278, the flowstream follows conduit 240 into the impact centrifugal separator 260. Upon detecting an end of the fraction, based upon time, detector signals, or collected volumes, the controller 400 may direct valve 270 to switch to the divert position with groove 278 connecting ports 272 and 274. The positioning arm 210 may then move to a subsequent collection vessel 220, 222, 224 and the collection process may repeat. As appreciated by one of skill in the art, the implementation of valve 270 is not limited to a rotary valve as shown, but may also include solenoid or other types of valve.

Fraction collector 300, if present, or other subsequent fraction collectors (not shown), may be directed by the controller 400 to collect fractions in a similar manner. After any and all fractions of a particular sample have been collected, subsequent samples may be injected by the injector 30 for detection and collection by fraction collectors 200, 300. In the action of collecting fractions, the fraction collectors may operate serially, collecting all fractions from a particular sample in collection vessels serially arranged within a particular collector before utilizing vials in subsequent collectors, or alternatively, may collect first fractions in a vessel in a first collector, and second fraction in subsequent collectors, or pooled where common fractions from multiple injections are collected in common (pooled) vessels. Also, a last collector may be used as a recovery or waste collector whereby all sample components not collected by upstream collectors are collected as a single, recovery fraction. The recovery fraction contents could then be subsequently re-injected in the event the true fraction of interest was not collected.

In an exemplary library (sequential) purification situation, injector 30 may utilize an automated liquid sampler to successively inject one or more samples for purification under the direction of the controller 400. The mobile phase delivery system comprising pumps 12 and 22 may operate isocratically or in a compositional, pressure, and/or flow gradient mode with each successive sample. The controller 400 may recognize the presence of desirable, collectable, sample components by monitoring signals, by time, or from one or more detectors 50, 52. With the recognition of each desired collectable component, the controller 400 would control fraction collector 200 to locate its positioning arm 210 over a fresh collection vessel 220, 222, 224 as needed and begin collection by switching the collect divert valve 270 to the collect position with groove 278 in fluid communication with valve port 276. Upon the recognition of the end of the elution of the desired component, the controller 400 would direct fraction collector 200 to switch the collect divert valve 270 to the divert position with groove 278 in fluid communication with valve port 272 and move the positioning arm 210 to the next fresh vessel 220, 222, 224 and thus regard the current vessel as used. This process may continue repetitively for each sample to be purified.

Figure 2:
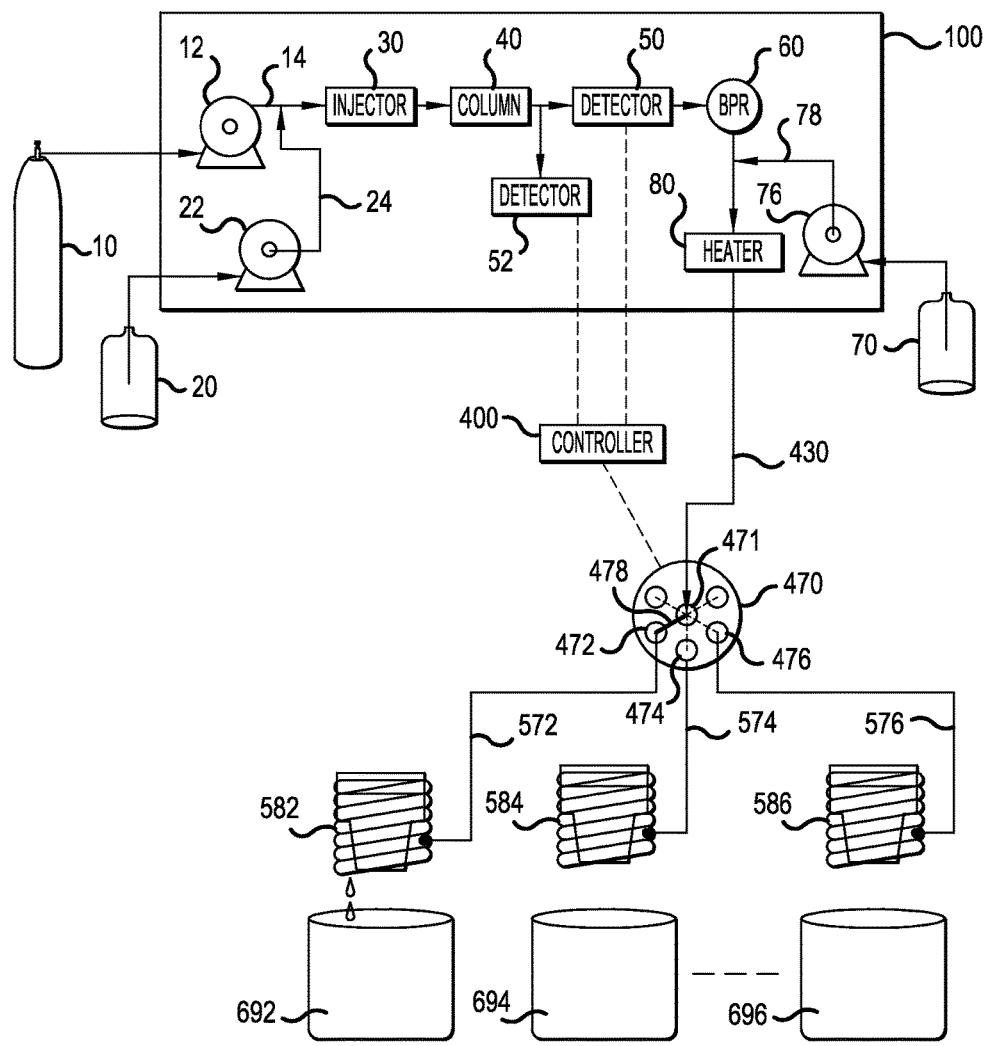
FIG. 2 is a simplified block diagram of another chromatography system including a plurality of uniquely addressable fraction collectors according to another embodiment.

Another embodiment is shown in FIG. 2. In this embodiment, multiple impact centrifugal separators of the present invention are utilized. The chromatography system 100 of FIG. 2 operates in the same manner as described in FIG. 1. However, FIG. 2. depicts a multi-port rotary collection valve 470. The collection valve 470 contains a common entry port 471 connected to a groove 478 that selectively connects to ports 472, 474, 476. Each exiting valve port 472, 474, 476 is connected to a conduit 572, 574, 576 respectively. The conduits 572, 574, 576 connect to the entry tubes of impact centrifugal separators 582, 584, 586 respectively. Each of the impact centrifugal separators 582, 584, 586 is physically positioned above collection vessels 692, 694, 696 respectively. The actual number of ports addressed by the collection valve 470 is dependent upon the valve chosen and could exemplarily contain 8, 10 or 12 individually addressable ports. Each valve port 472, 474, 476, and any additional selectable ports, respective conduits, separators, and vessels (not shown) may operate in the same manner.

Column effluent exiting the SFC system 100 through back pressure regulator 60 and optional heater 80 passes through conduit 430 into the common port 471 of collection valve 470. The rotary groove 478 is depicted connected to valve port 472. In this position the column effluent is directed through the collection valve to conduit 572 and into impact centrifugal separator 582. The impact centrifugal separator 582 will separate the liquid portions of the mobile phase from the gaseous portions as described herein. The liquid portions exiting separator 582 will be collected in vessel 692.

At the direction of controller 400, based upon signals from detectors 50, 52 or based upon time, the rotary collection valve 470 may switch to a different position. For example, groove 478 may rotate to connect common port 471 to exit port 474 thus directing column effluent from conduit 430 into conduit 574. Any effluent directed through conduit 574 will be separated in impact centrifugal separator 584 with the liquid portion being collected in the vessel 694. The controller 400 may further direct the collection valve 470 to switch, for example, to connect common port 471 to exit port 476 via groove 478. In this exemplary position, the column effluent travels from conduit 430 to conduit 576 entering impact centrifugal separator 586. The effluent entering impact centrifugal separator 586 is separated with the liquid portion being collected in collection vessel 696.

In an exemplary chiral (batch) based separation, the injector 30 will inject an aliquot of chiral sample into the mobile phase while the controller 400 may initially direct selection valve 470 to be positioned such that groove 478 connects common port 471 to exit port 474 allowing column effluent to be collected in vessel 694. Upon recognition by controller 400 that a first separated enantiomer is present in conduit 430 at common port 471, the controller 400 may direct selection valve 470 to switch groove 478 to exit port 472, thus collecting the first separated enantiomer in vessel 692. When the controller 400 recognizes the end of the elution of the first separated enantiomer, based upon signals from detectors 50, 52 or time, it may direct collection valve to return to exit port 474.

Upon recognition that a second separated enantiomer is present in conduit 430 at common port 471, the controller 400 may direct collection valve 470 to rotate groove 478 to connect common port 471 to exit port 476 thus directing column effluent through conduit 576 and impact centrifugal separator 586 to collect liquid portions in vessel 696. Upon recognition by controller 400 that the end of the elution of the second enantiomer has occurred, controller 400 may direct collection valve 470 to return grove 472 to return to exit port 474. This repetition of injection, recognition and collection of first and subsequently second enantiomers in respective vessels 692 and 696 may continue in a process known in the art as stacked injection.

The operation of the impact centrifugal separator (e.g., 260, 582, 584, 586) as taught in FIG. 1 and FIG. 2 is described as being located downstream of a valve to perform the fraction cut and immediately upstream of a final collection vessel. As should be clear from the present teachings, the impact centrifugal separator could be located in, and continuously separating, the incoming biphasic flowstream depositing the separated liquid into an intermediate vessel being actively drained. In such an embodiment, the liquid stream, emanating from the impact centrifugal separator, being collected in the intermediate vessel, is continuously pumped at a rate that prevents pooling within the intermediate vessel to a downstream liquid fraction collector. The continuous nature of the impact centrifugal separator and the deterministic time of travel through the impact centrifugal separator without broadening or merging of fluidic elements are especially suited for such downstream fraction cutting.

The exemplary operation of chromatographic separations having been shown using supercritical fluid chromatography (SFC) systems in FIGS. 1 and 2 yield an effluent similar in nature and compatible with the technique of supercritical fluid extraction (SFE). In both techniques, the effluent of a column or extraction chamber, respectively, containing carbon dioxide and organic modifiers entrained with sample constituents is directed through a back pressure regulator for expansion and subsequent collections. The upstream SFC and SFE flowstreams may interchangeably utilize downstream collection mechanisms and devices taught in relation to the embodiments described with reference to FIGS. 1 and 2.

The controller 400 may include a processor connected to the mobile phase pumping components, the sample introducing components, the separation components, the detection devices, and the fraction collectors for controlling aspects of the chromatography process. It is understood that the various connections between the controller and processor and the other components of the chromatography system 100 may be any type of wired and/or wireless connections enabling control communications, without departing from the scope of the present teachings. For example, the processor may control operation of pumps and pumping systems, pressure levels and/or mixture ratios in the sample introducing devices, as well as monitor various control parameters, such as flow rates, timing, and the like. In addition, the processor may receive data regarding sample detection (e.g., detected peaks, peak widths, resolution, efficiency, corresponding to separated analytes) from various detection devices. The received data may be displayed and/or stored for analysis, or used to adjust control elements relating to injection, pumping, or separation, for example.

Generally, the processor of the controller 400 may be implemented by a computer processor (e.g., of a personal computer (PC) or dedicated workstation), application specific integrated circuits (ASICs), field-programmable gate arrays (FPGAs), or combinations thereof, using software, firmware, hard-wired logic circuits, or combinations thereof. A computer processor, in particular, may be constructed of any combination of hardware, firmware or software architectures, and may include memory (e.g., volatile and/or nonvolatile memory) for storing executable software/firmware executable code that allows it to perform the various functions. In an embodiment, the computer processor may comprise a central processing unit (CPU), for example, executing an operating system.

Figure 3:
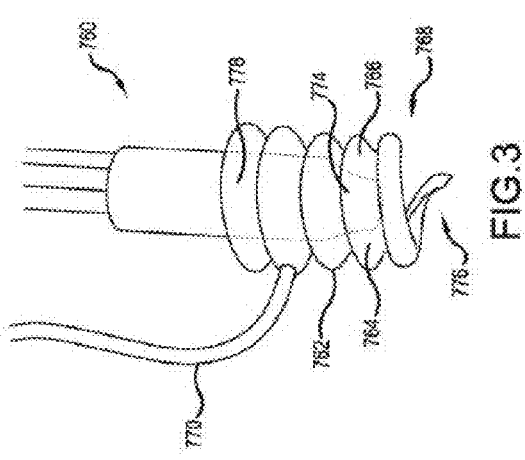
FIG. 3 is a side view of an embodiment of an impact centrifugal separator used in the fraction collection of FIGS. 1 and 2.
Figure 4:
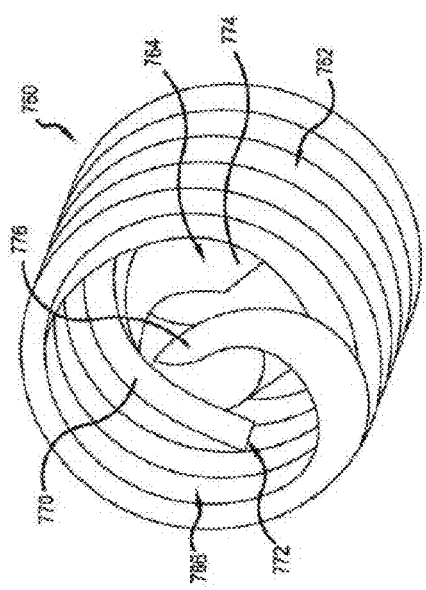
FIG. 4 is a bottom view of the impact centrifugal separator of FIG. 3.

With additional reference to FIGS. 3 and 4, further details of an embodiment of an impact centrifugal separator 760 as used in the fraction collection illustrated in FIGS. 1 and 2 (referenced as 260, 582, 584, and 586 therein), will now be described. The impact centrifugal separator 760 may operate continuously and sequentially on the incoming flowstream, passively separating waste gas from the liquid stream. Separation includes coalescing aerosolized liquid droplets entering the impact centrifugal separator 760 as a high velocity stream slowing into a low energy stream or series of drops exiting from the impact centrifugal separator 760. The impact centrifugal separator 760 may use only the kinetic energy of the incoming flowstream to traverse the impact centrifugal separator 760 without requiring any external gas flows or devices to create more uniform flows within the impact centrifugal separator 760. This continuous and sequential operation of separation of the incoming flowstream may provide the necessary and desirable time determinism of transit to allow accurate and precise timing of fraction cutting downstream of the impact centrifugal separator 760.

As discussed above, the impact centrifugal separator 760 is for use in collection of liquid portions of a bi-phasic flowstream in a supercritical fluid system such as an SFC or SFE system. The bi-phasic flowstream includes a gaseous (e.g. $CO_2$) and liquid component (e.g. methanol) as discussed in detail above. The impact centrifugal separator 760 includes a separator chamber 762, which is illustrated as a convoluted tube, for example. An interior space 764 is defined by the separator chamber 762 and is surrounded by a constraining spiral channel 766 that is open to such interior space 764. The constraining spiral channel 766 is located on an inner wall of the separator chamber 762. The constraining spiral channel 766 could be an integral part of the inner wall of the separator chamber 762 or it could be provided as a separate and distinct feature adjacent the inner wall of the separator chamber 762, for example.

The interior space 764 and constraining spiral channel 766 have a common exit 768 at a lower portion or bottom of the separator tube 762. As shown in FIGS. 3 and 4, the separator 760 has a horizontal orientation, with the downward exit along a vertical axis. Of course the separator chamber 762 with the constraining spiral channel 766 could be formed in other ways, such as by molding, for example. Constraining spiral channel 766 may have variable attributes such as shape, radius, pitch, size and depth. The shape of the constraining spiral channel 766 may include various concave examples including circular, parabolic, elliptical and rectangular profiles; with or without features such as lipped upper or lower edges. The shape of the interior space 764 may vary with increasing or decreasing diameter to alter the effective radius of the constraining spiral channel 766 over its length. The size of constraining spiral channel 766 can be constant or variable over its length. For example, a deepening constraining spiral channel 766 as it approaches the common exit 768 would favorably constrain the slowed liquid.

A flowstream director is defined here by an entry tube 770 having a distal end 772 configured to carry and focus the bi-phasic flowstream. The entry tube 770 enters the separator chamber 762 so that the bi-phasic flowstream leaving the distal end 772 is focused on a distinct region as it impacts a wall of the constraining spiral channel 766 at an angle that promotes coalescence of the liquid component within the constraining spiral channel 766. The entry tube 770 can go straight into the separator chamber 762, or one or more turns or wraps within the constraining spiral channel 766 can be included to provide some additional migration of liquid towards the outer wall of the entry tube 770 favorably altering the shape of the exit cone exiting the distal end of entry tube 770. By focusing and then constraining the coalesced liquid flow within the spiral channel, broadening of the fraction from fluid travel in non-uniform paths along a large surface such as a tube wall is avoided. The constraining spiral channel 766 is a downwardly spiraling channel and is configured to promote further coalescence of the liquid coalesced within the constraining spiral channel 766 as the liquid decelerates centripetally while traveling within the constraining spiral channel 766 after impact of the bi-phasic flowstream against the wall. The angle that the flowstream impacts the wall of the constraining spiral channel 766 creates a focused impact area for coalescing aerosol. The impact angle of the fluid exiting distal end 772 of entry tube 770 with a line tangential to the constraining spiral channel 766 should be exemplarily less than about 30° to promote rivulets and sliding impacts without rebound. Excessive impact angles, moving nearer perpendicular may favor droplet impacts with rebound, creating and splattering aerosolized components out of the constraining channel and into the exiting gaseous flow. Purely tangential angles may prevent the cone of bi-phasic aerosolized flow leaving distal end 772 of entry tube 770 from impacting the constraining spiral channel 766 and coalescing on the wall. Of course other flowstream director arrangements that focus the flowstream to impact the wall of the constraining spiral channel 766 are possible.

Unlike a cyclonic separator where aerosolized components are allowed entry to or specifically directed toward the interior portions of a space and allowed time to drift toward an outer surface, the liquid components of the present embodiments are focused by the flowstream director to immediately impact along the wall of the constraining spiral channel 766 and are generally not provided opportunity to navigate around the interior space 764 while drifting toward an outer wall. Following impact, momentum moves the liquid component along the constraining spiral channel 766. Centripetal deceleration causes the liquid to lose energy and velocity further coalescing into a large, slow stream. The slowed stream easily exits the constraining spiral channel 766 along a terminal edge positioned in the lower portion of the separator chamber 762 or optionally via the dripper 776 as drops. By moving through the separator chamber 762 without requiring additional energy to maintain flow, the liquid naturally exits when entry flow is stopped.

A central director 774 can be positioned in the interior space 764 of the separator tube 762, and configured to promote flow of the gaseous component of the bi-phasic flowstream around the director and toward the common exit 768 at the bottom of the separator tube 762. The central director 774 may not be required, and the present embodiments may operate without it. However, the central director 774 provides an additional constraint on the gaseous portion of the flowstream favoring swirling around the central director 774. In the event that a liquid droplet impacting the wall of the constraining spiral channel 766 were to rebound and enter into the gaseous stream, cyclonic like effects around the central director 774 would favor coalescence with the residual liquid constrained within the spiral channel 766. These cyclonic like effects, while advantageous, are secondary when compared to the coalescence provided by impact. An optional dripper 776 is in fluid communication with the constraining spiral channel 766 at the bottom of the separator chamber 762 in the common exit 768 and is configured to direct the coalesced liquid, for example, into a collection vessel (as shown in FIGS. 1 and 2). The dripper 776, when present, carries the slowed, coalesced liquid stream into the center of the exit 768 where the exiting gaseous flow can provide additional shear force on formed drops helping to blow them off of the dripper 776.

In an embodiment, the central director 774 is a tapered central director that is tapered in the direction of the common exit 768. Here, the entry tube 770 enters the separator chamber 762 adjacent a beginning of the taper of the tapered central director 774. An upper portion 778 of the central director 774 closes the top of the separator chamber 762. In an embodiment, the entry tube 770 enters the separator chamber 762 and follows around a portion of the constraining spiral channel 766, e.g. for part or all of a rotation, before the distal end 772 where the bi-phasic flowstream leaves and impacts the wall of the constraining spiral channel 766. In an embodiment, the central director 774 could be heated to reduce or eliminate some effects of cold flow at the entry tube 770.

In an embodiment, the constraining spiral channel 766 may have a variable pitch that is significantly nearer vertical at the dripper 776 in the common exit 768. Also, in an embodiment, a funnel may be included below the impact centrifugal separator 760 to receive the coalesced liquid from the terminal edge of the constraining spiral channel 766 or optionally the dripper 776. Further embodiments of the impact centrifugal separator 760 may include other improvements such as heating the impact centrifugal separator 760, the central director 774, or the entering bi-phasic flowstream. Such heating reduces any potential for condensation of ambient moisture. The attribute of a single entry tube 770 to focus the flowstream to impact the constraining spiral channel 766 at a single impact region prevents broadening that would inherently occur if the incoming flowstream is passed through or along a large area surface. The focused point of entry into the constraining spiral channel 766 via the entry tube 770 further prevents intermixing of fluidic elements that would occur if droplets were allowed entry into the exiting flowstream at various or multiple positions within the constraining spiral channel 766. While a single constraining spiral channel 766 and entry tube 770 has been taught, multiple instances of the constraining spiral channel 766 and entry tube 770 can be implemented surrounding the interior space 764 for increasing the flow rate capacity of the impact centrifugal separator 760 without departing from the scope of the present teachings. Multiple, parallel, instances of the constraining spiral channel 766 and entry tube 770 may require that the constraining spiral channels' 766 shape and length, and the entry tube's 770 internal diameter and flow rate be consistent to maintain the same liquid flow rate and transit time through each of the constraining spiral channels 766.

Figure 6:
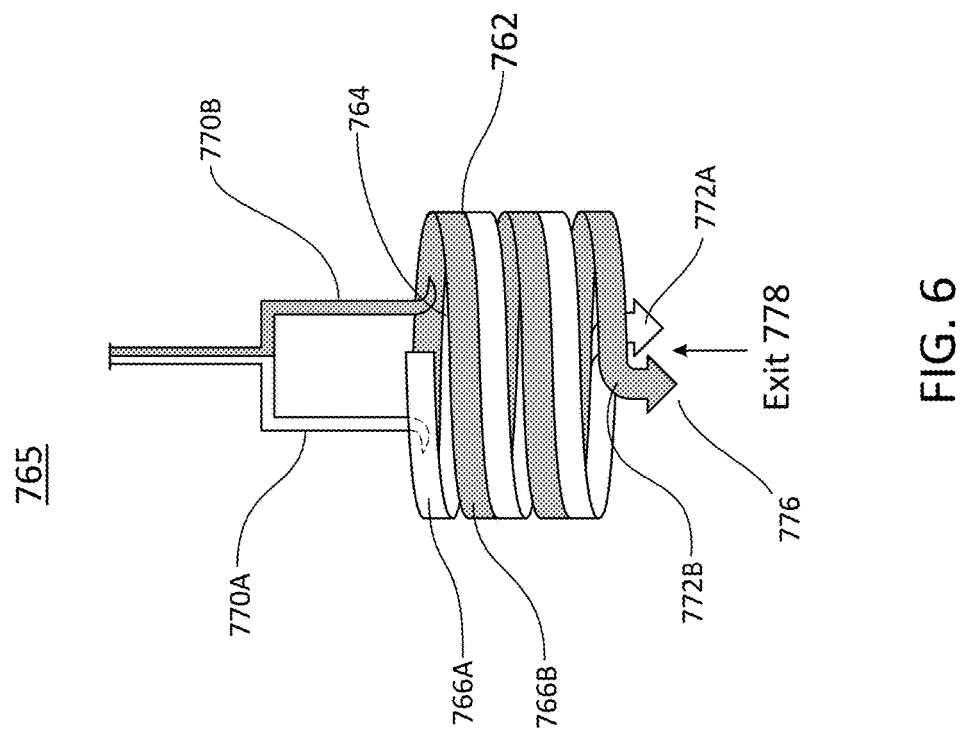
FIG. 6 is a schematic view of an impact centrifugal separator according to another embodiment.

FIG. 6 illustrates an example of an impact centrifugal separator 765 that includes multiple instances of a constraining spiral channel and entry tube. The impact centrifugal separator 765 includes a separator chamber 762 and interior space 764 defined by the separator chamber 762. In the present embodiment, the interior space 764 is surrounded by two or more constraining spiral channels 766A and 766B that are open to such interior space 764. The constraining spiral channels 766A and 766B are located on an inner wall of the separator chamber 762. The interior space 764 and constraining spiral channels 766A and 766B have a common exit 768 at a lower portion or bottom of the separator tube 762. In the present embodiment, the flowstream director is defined by two or more entry tubes 770A and 770B having respective distal ends 772A and 772B. The entry tubes 770A and 770B are configured to carry and focus respective bi-phasic flowstreams in the manner discussed above. Thus, the entry tubes 770A and 770B enter the separator chamber 762 so that the bi-phasic flowstreams leaving the respective distal ends 772A and 772B are focused on respective distinct regions as the bi-phasic flowstreams impact respective walls of the constraining spiral channels 766A and 766B at an angle that promotes coalescence of the liquid component within the constraining spiral channels 766A and 766B. As described above, the entry tubes 770A and 770B can go straight into the separator chamber 762, or one or more turns or wraps within the constraining spiral channels 766A and 766B can be included to provide some additional migration of liquid towards the respective outer walls of the entry tubes 770A and 770B, thereby favorably altering the shape of the exit cone exiting the respective distal ends 772A and 772B of the entry tubes 770A and 770B. As described above, the constraining spiral channels 766A and 766B may be downwardly spiraling channels and are configured to promote further coalescence of the liquid coalesced within the constraining spiral channels 766A and 766B as the liquid decelerates centripetally while traveling within the constraining spiral channels 766A and 766B after impact of the bi-phasic flowstreams against the respective walls. The angle at which the flowstreams impact the walls of the constraining spiral channels 766A and 766B creates a focused impact area for coalescing aerosol. The slowed streams easily exit the respective constraining spiral channels 766A and 766B along respective terminal edges positioned in the lower portion of the separator chamber 762 or optionally via the dripper 776 as drops, as indicated by arrows in FIG. 6 and as described above. The impact centrifugal separator 765 may have one or more of the other attributes described above in conjunction with FIGS. 3 and 4.

Figure 5:
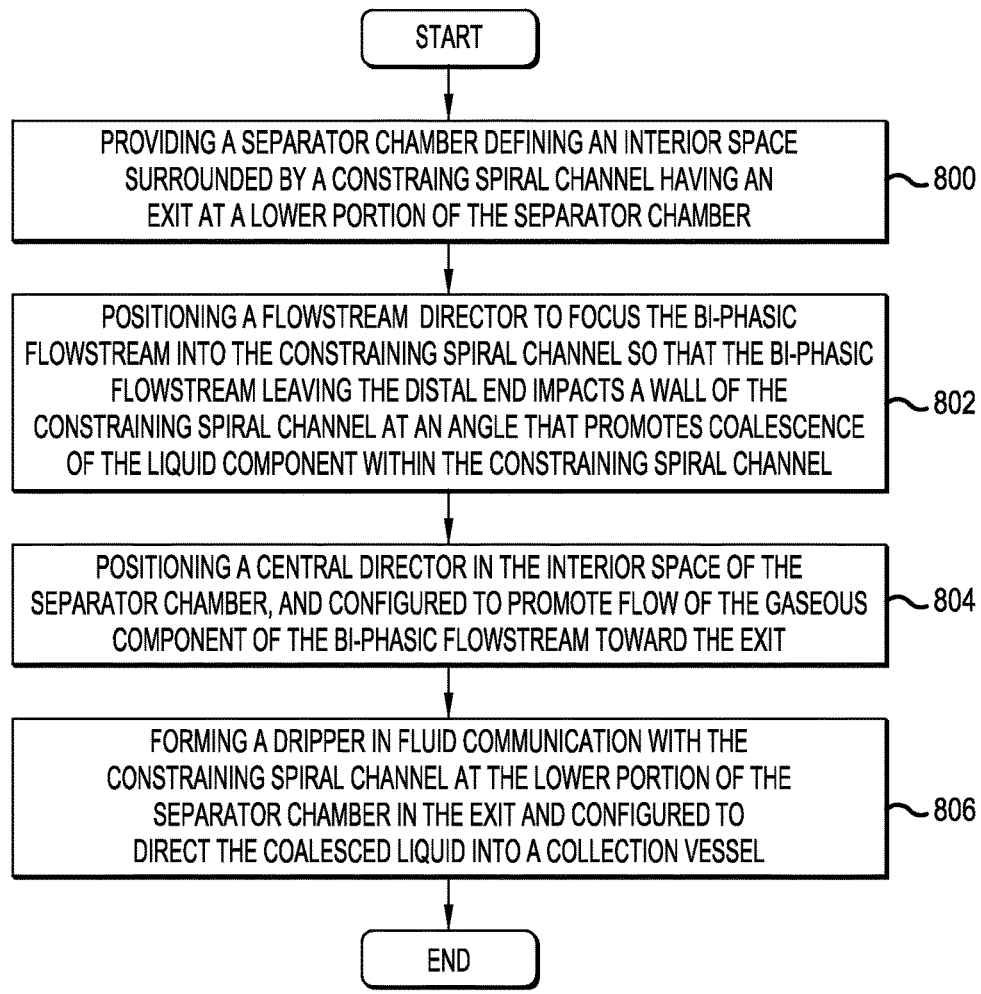
FIG. 5 is a flow diagram illustrating a method of making an impact centrifugal separator according to a representative embodiment.

A method aspect of the present embodiments will be described with reference to the flowchart of FIG. 5. The method is for making an impact centrifugal separator 760 for use in collection of liquid portions of a bi-phasic flowstream in a supercritical fluid system. Again, the bi-phasic flowstream includes a gaseous and liquid component. The method begins and includes providing (block 800) a separator chamber 762 defining an interior space 764 surrounded by a constraining spiral channel 766 that is open to the interior space 764, the constraining spiral channel 766 located on an inner wall of the separator chamber 762, the interior space 764 having an exit 768 at a lower portion or bottom of the separator chamber 762. The method includes positioning (block 802) a flowstream director (e.g. entry tube 770, having a distal end 772) to focus the bi-phasic flowstream into the constraining spiral channel 766 so that the bi-phasic flowstream leaving the distal end 772 impacts a wall of the constraining spiral channel 766 at an angle that promotes coalescence of the liquid component within the constraining spiral channel 766.

As discussed above, the constraining spiral channel 766 is configured to promote further coalescence of the liquid portions during centripetal deceleration within the constraining spiral channel 766 after impact of the bi-phasic flowstream against the wall. The method may include positioning (block 804) a central director 774 in the interior space 764 of the separator chamber 762, and configured to promote flow of the gaseous component of the bi-phasic flowstream toward a common exit 768 at the bottom of the separator tube 762. At block 806, the method may include forming a dripper 776 in fluid communication with the constraining spiral channel 766 at the bottom of the separator chamber 762 in the common exit 768 and configured to direct the coalesced liquid into a collection vessel (as shown in FIGS. 1 and 2).

Collection of fractions is achieved with an open tubular impact centrifugal separator of a fraction collector without requiring a contained vessel to separate the $CO_2$, or external pressure control to reduce aerosol formation.

One of ordinary skill in the art appreciates that many variations that are in accordance with the present teachings are possible and remain within the scope of the appended claims. These and other variations would become clear to one of ordinary skill in the art after inspection of the specification, drawings and claims herein. The invention therefore is not to be restricted except within the spirit and scope of the appended claims.

What is claimed:

1. An impact centrifugal separator for use in collection of liquid portions of a bi-phasic flowstream in a supercritical fluid system, the bi-phasic flowstream including a gaseous component and a liquid component, the impact centrifugal separator comprising:

a separator chamber defining an interior space, the separator chamber comprising an inner wall, a spiral channel defined on the inner wall and surrounding and open to the interior space, and an open lower portion defining an exit for the gaseous component and the liquid component; and a flow stream director comprising a single entry tube entering the separator chamber, the entry tube comprising a single distal end positioned in the interior space in communication with the spiral channel, wherein the distal end is positioned and oriented such that the entry tube focuses the bi-phasic flowstream on a single impact region of the spiral channel so that the bi-phasic flowstream immediately impacts a wall of the spiral channel at a focused impact area after leaving the distal end, and impacts the wall of the spiral channel at an angle to the wall of the spiral channel that promotes coalescence of the liquid component within the spiral channel, and wherein the entry tube follows around a portion of the spiral channel before the distal end of the entry tube directs the bi-phasic flowstream to impact the wall of the spiral channel.

2. The impact centrifugal separator of claim 1, further comprising a tapered central director positioned in the interior space of the separator chamber, and configured to promote flow of the gaseous component of the bi-phasic flowstream toward the exit at the lower portion of the separator chamber.

3. The impact centrifugal separator of claim 2, wherein the tapered central director comprises an upper portion defining a closed top of the separator chamber.

4. The impact centrifugal separator of claim 1, wherein the spiral channel comprises a variable pitch or a variable radius configured to promote further coalescence of the liquid component during centripetal deceleration within the spiral channel after impact of the bi-phasic flowstream against the wall of the spiral channel.

5. The impact centrifugal separator of claim 1, further comprising a dripper in fluid communication with the spiral channel at the lower portion of the separator chamber in the exit and configured to direct the coalesced liquid into a collection vessel.

6. The impact centrifugal separator of claim 1, wherein the spiral channel has at least one variable characteristic selected from the group consisting of: shape, radius, pitch, size, and depth.

7. The impact centrifugal separator of claim 1, wherein the distal end is positioned and oriented such that the bi-phasic flowstream impacts the wall of the spiral channel at a non-tangential angle to the wall of the spiral channel.

8. The impact centrifugal separator of claim 1, wherein:
the spiral channel is one of a plurality of parallel spiral channels, each spiral channel defined on the inner wall and surrounding and open to the interior space; and
the entry tube is one of a plurality of entry tubes entering the separator chamber and comprising respective single distal ends positioned in the interior space in communication with the respective spiral channels, wherein the distal ends are positioned and oriented such that the respective entry tubes focus respective bi-phasic flowstreams on respective single impact regions of the respective spiral channels so that the bi-phasic flowstreams immediately impact respective walls of the respective spiral channels at respective focused impact areas after leaving the respective distal ends.

9. An impact centrifugal separator for use in collection of liquid portions of a bi-phasic flowstream in a supercritical fluid system, the bi-phasic flowstream including a gaseous component and a liquid component, the impact centrifugal separator comprising:

a separator chamber defining an interior space, the separator chamber comprising an inner wall, a spiral channel defined on the inner wall and surrounding and open to the interior space, and an open lower portion defining an exit for the gaseous component and the liquid component;

a flowstream director comprising a single entry tube entering the separator chamber, the entry tube comprising a single distal end positioned in the interior space in communication with the spiral channel, wherein the distal end is positioned and oriented such that the entry tube focuses the bi-phasic flowstream on a single impact region of the spiral channel so that the bi-phasic flowstream immediately impacts a wall of the spiral channel at a focused impact area after leaving the distal end, and impacts the wall of the spiral channel at an angle to the wall of the spiral channel that promotes coalescence of the liquid component within the spiral channel; and a tapered central director positioned in the interior space of the separator chamber, and configured to promote flow of the gaseous component of the bi-phasic flowstream toward the exit at the lower portion of the separator chamber.

10. The impact centrifugal separator of claim 9, wherein the entry tube follows around a portion of the spiral channel before the distal end of the entry tube directs the bi-phasic flow stream to impact the wall of the spiral channel.

11. The impact centrifugal separator of claim 9, wherein the tapered central director comprises an upper portion defining a closed top of the separator chamber.

12. The impact centrifugal separator of claim 9, further comprising a dripper in fluid communication with the spiral channel at the lower portion of the separator chamber in the exit and configured to direct the coalesced liquid into a collection vessel.

13. The impact centrifugal separator of claim 9, wherein the distal end is positioned and oriented such that the bi-phasic flowstream impacts the wall of the spiral channel at a non-tangential angle to the wall of the spiral channel.

14. The impact centrifugal separator of claim 9, wherein:
the spiral channel is one of a plurality of parallel spiral channels, each spiral channel defined on the inner wall and surrounding and open to the interior space; and
the entry tube is one of a plurality of entry tubes entering the separator chamber and comprising respective single distal ends positioned in the interior space in communication with the respective spiral channels, wherein the distal ends are positioned and oriented such that the respective entry tubes focus respective bi-phasic flowstreams on respective single impact regions of the respective spiral channels so that the bi-phasic flowstreams immediately impact respective walls of the respective spiral channels at respective focused impact areas after leaving the respective distal ends.

15. An impact centrifugal separator for use in collection of liquid portions of a bi-phasic flowstream in a supercritical fluid system, the bi-phasic flowstream including a gaseous component and a liquid component, the impact centrifugal separator comprising:

a separator chamber defining an interior space, the separator chamber comprising an inner wall, a spiral channel defined on the inner wall and surrounding and open to the interior space, and an open lower portion defining an exit for the gaseous component and the liquid component;
a flow stream director comprising a single entry tube entering the separator chamber, the entry tube comprising a single distal end positioned in the interior space in communication with the spiral channel, wherein the distal end is positioned and oriented such that the entry tube focuses the bi-phasic flowstream on a single impact region of the spiral channel so that the bi-phasic flowstream immediately impacts a wall of the spiral channel at a focused impact area after leaving the distal end, and impacts the wall of the spiral channel at an angle to the wall of the spiral channel that promotes coalescence of the liquid component within the spiral channel; and
a dripper in fluid communication with the spiral channel at the lower portion of the separator chamber in the exit and configured to direct the coalesced liquid into a collection vessel.

16. The impact centrifugal separator of claim 15, wherein the entry tube follows around a portion of the spiral channel before the distal end of the entry tube directs the bi-phasic flow stream to impact the wall of the spiral channel.

17. The impact centrifugal separator of claim 15, further comprising a tapered central director positioned in the interior space of the separator chamber, and configured to promote flow of the gaseous component of the bi-phasic flowstream toward the exit at the lower portion of the separator chamber.

18. The impact centrifugal separator of claim 17, wherein the tapered central director comprises an upper portion defining a closed top of the separator chamber.

19. The impact centrifugal separator of claim 15, wherein the distal end is positioned and oriented such that the bi-phasic flowstream impacts the wall of the spiral channel at a non-tangential angle to the wall of the spiral channel.

20. The impact centrifugal separator of claim 15, wherein:
the spiral channel is one of a plurality of parallel spiral channels, each spiral channel defined on the inner wall and surrounding and open to the interior space; and
the entry tube is one of a plurality of entry tubes entering the separator chamber and comprising respective single distal ends positioned in the interior space in communication with the respective spiral channels, wherein the distal ends are positioned and oriented such that the respective entry tubes focus respective bi-phasic flowstreams on respective single impact regions of the respective spiral channels so that the bi-phasic flowstreams immediately impact respective walls of the respective spiral channels at respective focused impact areas after leaving the respective distal ends.

* * * * *